(12) United States Patent
Brahm et al.

(10) Patent No.: US 9,789,138 B1
(45) Date of Patent: Oct. 17, 2017

(54) NEURAL REPAIR CONSTRUCT AND METHOD OF USE

(71) Applicant: BioDlogics, LLC, Cordova, TN (US)

(72) Inventors: Timothy B. Brahm, Germantown, TN (US); Greg Brophy, Knoxville, TN (US)

(73) Assignee: BioDLogics, LLC, Cordova, TN (US)

( * ) Notice: Subject to any disclaimer, the term of this patent is extended or adjusted under 35 U.S.C. 154(b) by 94 days.

(21) Appl. No.: 14/194,926

(22) Filed: Mar. 3, 2014

Related U.S. Application Data (60) Provisional application No. 61/773,249, filed on Mar. 6, 2013.

(51) Int. Cl.
*A61K 35/50* (2015.01)

(52) U.S. Cl.
CPC ................................. *A61K 35/50* (2013.01)

(58) Field of Classification Search
CPC ...................................................... A61K 35/50
See application file for complete search history.

(56) References Cited

U.S. PATENT DOCUMENTS

| | | | |
|---|---|---|---|
| 4,120,649 A | 10/1978 | Schechter | |
| 4,361,552 A | 11/1982 | Baur, Jr. | |
| 4,674,488 A | 6/1987 | Campbell | |
| 4,894,063 A | 1/1990 | Nashef | |
| 5,607,590 A | 3/1997 | Shimizu | |
| 5,618,312 A | 4/1997 | Yui | |
| 6,152,142 A | 11/2000 | Tseng | |
| 6,254,637 B1 | 7/2001 | Lee | |
| 6,326,019 B1 | 12/2001 | Tseng | |
| 2001/0053839 A1 | 12/2001 | Noishiki | |
| 2003/0187515 A1 | 10/2003 | Hariri | |
| 2003/0225355 A1 | 12/2003 | Butler | |
| 2004/0048796 A1 | 3/2004 | Hariri | |
| 2007/0031471 A1 | 2/2007 | Peyman | |
| 2007/0038298 A1 | 2/2007 | Sulner | |
| 2008/0044848 A1 | 2/2008 | Heidaran | |
| 2008/0046095 A1 | 2/2008 | Daniel | |

(Continued)

FOREIGN PATENT DOCUMENTS

| | | |
|---|---|---|
| EP | 0781564 A2 | 7/1997 |
| WO | WO 93/10722 | 6/1993 |

(Continued)

OTHER PUBLICATIONS

Gajiwala et al., Evaluation of lyophilized, gamma-irradiated amnion as a biological dressing. Cell Tissue Bank, vol. 5, No. 2 (2004) pp. 73-80.*

(Continued)

*Primary Examiner* — Kara Johnson
(74) *Attorney, Agent, or Firm* — Brinks Gilson & Lione (57) ABSTRACT

A neural repair construct fabricated from human birth tissue comprising at least one cross-linked amniotic membrane, or at least one cross-linked chorionic membrane, or at least one amniotic membrane, or at least one chorionic membrane, or any combination thereof wherein the membrane(s) is/are treated with at least one alcohol composition followed by terminal sterilization is provided. Methods of processing a membrane to form a neural repair construct, methods of repairing a nerve and associated kits are also provided.

11 Claims, 5 Drawing Sheets

(56) References Cited

U.S. PATENT DOCUMENTS

| | | |
|---|---|---|
| 2008/0131522 A1 | 6/2008 | Liu |
| 2008/0193554 A1 | 8/2008 | Dua |
| 2008/0274184 A1 | 11/2008 | Hunt |
| 2009/0208551 A1 | 8/2009 | Kim |
| 2010/0104539 A1 | 4/2010 | Spencer |
| 2010/0106233 A1 | 4/2010 | Deeken |
| 2011/0129520 A1 | 6/2011 | Bogdansky |
| 2011/0189301 A1 | 8/2011 | Yang |
| 2012/0009644 A1 | 1/2012 | Goldstein |
| 2012/0009679 A1 | 1/2012 | Walsh |
| 2012/0020933 A1* | 1/2012 | Young et al. ............... 424/93.7 |
| 2012/0078378 A1 | 3/2012 | Spencer |
| 2012/0083900 A1 | 4/2012 | Samaniego et al. |
| 2013/0156863 A1* | 6/2013 | Tseng et al. ................ 424/583 |
| 2014/0067058 A1* | 3/2014 | Koob .................... A61L 27/14 623/4.1 |

FOREIGN PATENT DOCUMENTS

| | | |
|---|---|---|
| WO | 2009044408 A1 | 4/2009 |
| WO | 2012003377 A2 | 1/2012 |
| WO | 2012112417 A2 | 8/2012 |
| WO | 2012112441 A1 | 8/2012 |

OTHER PUBLICATIONS

Kubo et al., Immunogenicity of human amniotic membrane in experimental xenotransplantation. Immunology and Microbiology, vol. 42 (Jun. 2001) pp. 1539-1546.*

Rolls, G., An Introduction to Specimen Processing. Leica Biosystems, 2016 [retrieved on Sep. 12, 2016]. Retrieved from the Internet <URL: http://www.leicabiosystems.com/pathologyleaders/an-introduction-to-specimen-processing/>.*

* cited by examiner

NEURAL REPAIR CONSTRUCT AND METHOD OF USE

CROSS-REFERENCE TO RELATED APPLICATIONS

This application claims priority to U.S. Provisional Patent Application No. 61/773,249 filed Mar. 6, 2013, the content of which is incorporated herein in its entirety.

FIELD OF THE INVENTION

The present invention is directed to a neural repair construct composed of human birth tissue material recovered aseptically from human birth tissue, as well as methods of processing the same to prepare a neural repair construct and methods of using the same.

BACKGROUND OF THE INVENTION

The nervous system serves as the body control center and communications electrical-chemical wiring network. As a key homeostatic regulatory and coordinating system, it detects, interprets, and responds to changes in internal and external conditions. The nervous system integrates countless bits of information and generates appropriate reactions by sending electrochemical impulses through nerves to effector organs, such as muscles and glands. The brain and spinal cord are the central nervous system (CNS); the connecting nerve processes to effectors and receptors serve as the peripheral nervous system (PNS). Special sense receptors provide for taste, smell, sight, hearing, and balance. Nerves carry all messages exchanged between the CNS and the rest of the body.

A nerve is an enclosed, cable-like bundle of axons (long, slender projections of neurons) in the peripheral nervous system. Nerves provide a common pathway for the electrochemical nerve impulses that are transmitted along each of the axons to peripheral organs. Each nerve is covered externally by a dense sheath of connective tissue known as the epineurium. Underlying the epineurium is a layer of flat cells, the perineurium, which forms a complete sleeve around a bundle of axons. Perineurial septae extend into the nerve and subdivide it into several bundles of fibers. Surrounding each fiber is the endoneurium, which consists of an inner sleeve of material called the glycocalyx and an outer, delicate, meshwork of collagen fibers. Damage to nerves can be caused by physical injury or swelling (e.g. carpal tunnel syndrome), autoimmune diseases (e.g. Guillain-Barré syndrome), infection (neuritis), diabetes or failure of the blood vessels surrounding the nerve.

Repairing damaged nerves is hampered by several factors, including damage to the protective sheathing that surrounds nerves, gaps between the proximal and distal stumps of severed nerves and the limited ability of damaged nerves to regenerate. Tubes or conduits for guiding peripheral nerve regeneration are commonly made of materials such as polylactide, polylactide/polyglycolide copolymers, acrylic copolymers, performed mesothelial tubes or various other synthetic polyesters. The shortcomings of using a tube or conduit made of these materials include, for example, immune response, induction of scar tissue, and difficulty in application.

Thus, there remains a need for materials and techniques that provide a safe, effective means of repairing damaged or otherwise traumatized nerves in the body.

SUMMARY OF THE INVENTION

The present invention is generally directed to a neural repair construct and processes for producing the neural repair construct. The neural repair construct of the present invention has unique properties that aid in the restoration and regeneration of severed or otherwise damaged nerves in the body.

According to one aspect, a neural repair construct is provided that includes at least one cross-linked amniotic membrane, or at least one cross-linked chorionic membrane, or at least one amniotic membrane, or at least one chorionic membrane, or a combination thereof. According to one embodiment, the cross-linked membrane(s) is/are treated with a cross-linking solution comprising from about 0.05% to about 3% glutaraldehyde. According to one embodiment, the membrane(s) is/are treated with at least one alcohol composition followed by terminal sterilization to form a neural repair construct. The alcohol composition comprises from about 90% to about 100% ethanol. Terminal sterilization is carried out via gamma irradiation or electron beam irradiation.

According to another aspect, a method of preparing a membrane for a neural repair construct is provided. The method includes the steps of:

(a) obtaining amniotic membrane, chorionic membrane, or both amniotic and chorionic membrane from a seronegative, healthy human via Cesarean section or vaginal delivery;

(b) immersing the membrane in a basin containing a sterile saline solution;

(c) agitating the basin to liberate excess blood and fluids from the membrane;

(d) rinsing the membrane with a sterile saline solution;

(e) optionally, covering the membrane with a substrate on both the fetal membrane side and the maternal membrane side;

(f) optionally, immersing the membrane in a preservative solution for a period of up to about 20 minutes, wherein the preservative solution comprises from about 0.05% to about 3% glutaraldehyde, an alcohol composition or a combination thereof;

(g) optionally, rinsing the membrane with a sterile saline solution;

(h) optionally, soaking the membrane in a sterile saline solution;

(i) immersing the membrane in an alcohol composition for a period of from about 24 hours to about 384 hours;

(j) removing the optional substrate from both the fetal membrane side and the maternal membrane side;

(k) spreading the membrane on a flat, dry and sterile surface;

(l) allowing the membrane to air dry completely at ambient temperature for a period of up to three hours;

(m) cutting the membrane to a predetermined size;

(n) optionally, placing the fetal side of the membrane directly onto a pre-cut substrate; and (o) forming a substantially cylindrical, hollow neural repair construct.

The method of preparing a membrane for a neural repair construct may further include the steps of packaging the neural repair construct in a dry state or in a wet state and terminally sterilizing the packaged neural repair construct using irradiation. According to one embodiment, the method may further include the step of removing the chorionic membrane via blunt dissection and discarding the chorionic membrane. According to another embodiment, the method may further include the step of placing the membrane in sterile saline solution for a period of up to about five days between steps (a) and (b). In such an embodiment, the sterile saline solution includes from about 0.9% to about 20% NaCl. According to one embodiment, the sterile saline solution in step (b) may include from about 0.9% to about 20% NaCl. According to one embodiment, the sterile saline solution in steps (d) and (g) may also include from about 0.9% to about 20% NaCl. According to one embodiment, the rinse steps (d) and (g) are conducted for a maximum time period of five minutes. According to one embodiment, the sterile saline solution in step (h) comprises from about 0.9% to about 20% NaCl, and the soak in step (h) is conducted for a maximum period of about 35 minutes. According to one embodiment, the preservative solution comprises 0.1% glutaraldehyde. According to one embodiment, the alcohol composition in steps (f) and (i) each include from about 90% to about 100% ethanol. According to another embodiment, the alcohol composition in steps (f) and (i) comprises 95.5% ethanol. According to another embodiment, the alcohol composition in steps (f) and (i) comprises 100% ethanol.

According to one embodiment, the method further includes the step of treating the membrane with an oxidizer between steps (a) and (b). According to one embodiment, the oxidizer is hydrogen peroxide and the step of treating the membrane further includes the steps of:

(a) rinsing the membrane with about 120 ml of sterile isotonic solution per gram of membrane for a time period of up to about ten minutes;

(b) treating the membrane with about 60 ml of hydrogen peroxide per gram of membrane for a time period of up to about ten minutes; and (c) rinsing the membrane with about 120 ml of sterile isotonic solution per gram of membrane for a time period of up to about ten minutes.

According to another aspect, a neural repair construct is provided that is produced by the aforementioned method. According to one embodiment, the ethanol residual levels determined by gas chromatography are not detected at the corresponding minimum report limit. According to one embodiment, the glutaraldehyde residual levels determined by gas chromatography are not detected at the corresponding minimum reporting limit.

According to another aspect, a method of repairing a severed nerve is provided. The method includes the steps of providing a neural repair construct as provided herein, securing a first nerve stump to a first end of the construct, and securing a second nerve stump to a second, opposing end of the construct. According to one embodiment, the step of securing the first and second nerve stumps to the opposing ends of the construct is accomplished by at least one epineural grasping stitch.

According to another aspect, a kit for use by a medical professional is provided. According to one embodiment, the kit includes one or more packaged and sterilized neural repair constructs as provided herein and at least one set of instructions. The kit may also include at least one composition or device for delivering, fastening or fixing the neural repair construct on or around a nerve.

DETAILED DESCRIPTION OF THE INVENTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise. As used in the specification and in the appended claims, the words "optional" or "optionally" mean that the subsequently described event or circumstance can or cannot occur. For example, the phrase "optionally soaking the membrane" means that the soaking step may or may not be performed.

As used herein, the term "human birth tissue" includes, but is not limited to, elements of the placental organ such as, for example, the placental globe, umbilical cord, umbilical cord blood, associated membranes (chorionic membrane and amniotic membrane), and other placental gelatins, fluids, cells and extracellular material obtained from a seronegative, healthy human.

As used herein, the term "construct" refers to a substantially cylindrical, elongated hollow tube or sheath-like structure formed from human birth tissue material according to the methods provided herein.

As used herein, the term "repair" refers to the process of restoring, regenerating, or otherwise returning one or more damages tissues (e.g., nerves) to a substantially original, functioning state.

The present invention generally relates to the use of at least one cross-linked amniotic membrane, or at least one cross-linked chorionic membrane, or at least one amniotic membrane, or at least one chorionic membrane, or a combination thereof, to form a neural repair construct. In a preferred embodiment, the neural repair construct provides a means of restoration and regeneration for one or more damaged nerves in the body. In certain embodiments, the neural repair construct is fully resorbed by the body after placement. In other embodiments, the neural repair construct remains intact on or around the damaged nerve. The neural repair construct may be used to repair any peripheral nerve throughout the body. By forming the construct from human birth tissue material, the construct also prevents scar formation on the nerve sheath (e.g., epineurium), scarring within the nerve (e.g., perineurium and endoneurium), and tethering of the nerve to surrounding tissue. Once implanted, the construct also reduces inflammation, minimizes the potential for nerve entrapment and provides a protective conduit for axonal regrowth and regeneration across a nerve gap. The construct as provided herein is flexible enough to accommodate movement of joints and associated tendons, yet strong enough to retain a substantially round, cylindrical shape, thereby resisting occlusive forces of any surrounding tissues.

Cross-linked and non-cross-linked amniotic and chorionic membranes may be utilized alone or in various combinations or layers to form the neural repair construct. The present disclosure provides methods of preparing a neural repair construct that includes at least one cross-linked amniotic membrane, or at least one cross-linked chorionic membrane, or at least one amniotic membrane, or at least one chorionic membrane, or a combination thereof. Thus, the term "membrane" refers to a cross-linked amniotic membrane, a cross-linked chorionic membrane, an amniotic membrane, a chorionic membrane or any combination thereof.

According to one embodiment, the membrane(s) is/are cross-linked by treating the membrane(s) with a glutaraldehyde composition. The glutaraldehyde composition includes glutaraldehyde typically in an amount of from about 0.05% to about 3%. The resulting membrane(s) is/are treated with at least one alcohol composition and then terminally sterilized to form a neural repair construct.

According to one embodiment, the membrane(s) is/are not cross-linked. The membrane(s) is/are treated with one alcohol composition that include typically from about 90% to about 100% ethanol. According to an alternative embodiment, the membrane(s) is/are treated with at least two alcohol compositions that each include typically from about 90% to about 100% ethanol. The resulting membrane(s) is/are terminally sterilized to form a neural repair construct.

Figures 1A, 1B:
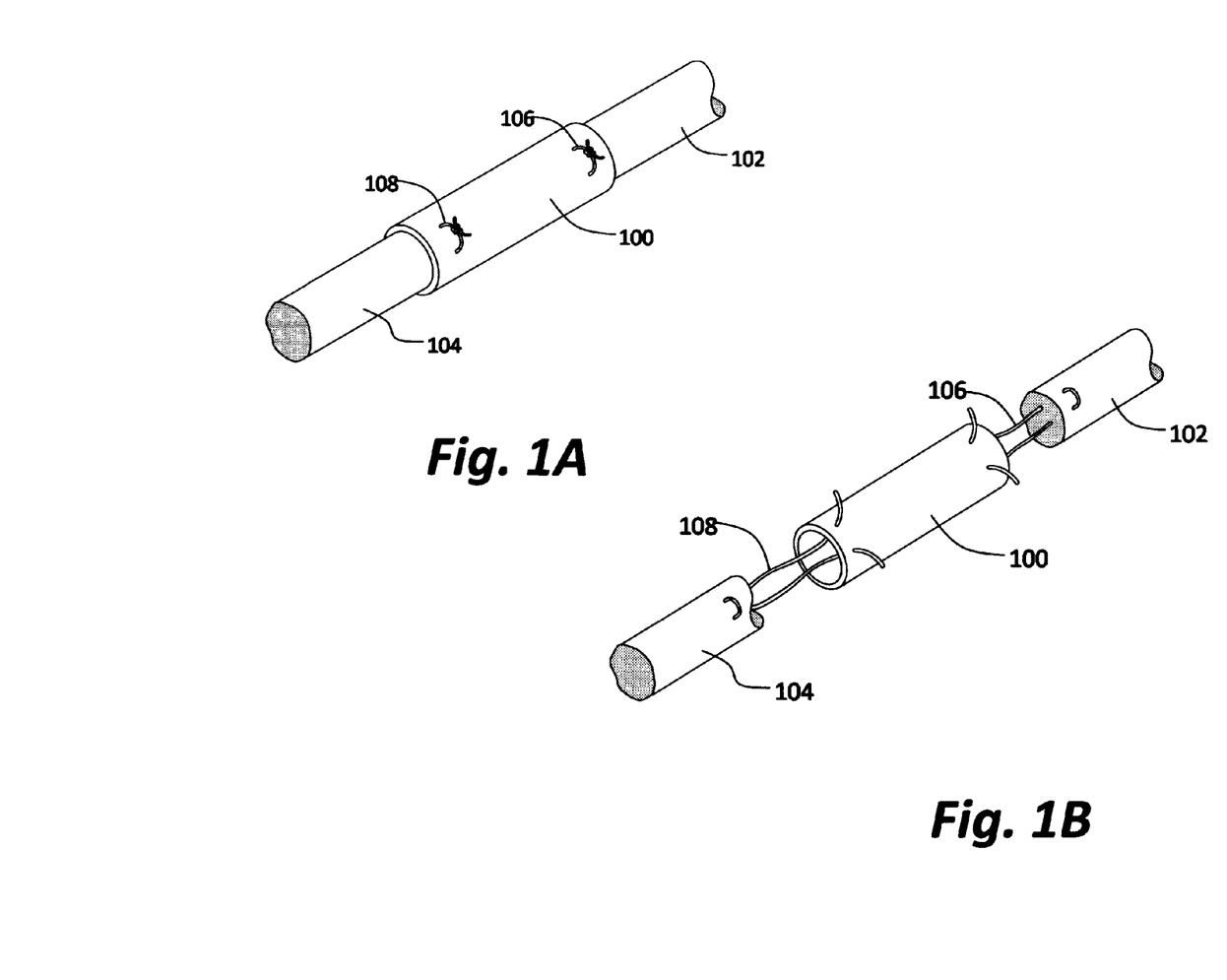
FIG. 1A illustrates a perspective view of a neural repair construct according to one embodiment.
FIG. 1B illustrates a perspective view of the placement of a neural repair construct according to one embodiment.

FIG. 1A provides a perspective view of a neural repair construct 100 according to one embodiment. As illustrated, the construct 100 is secured to a first nerve stump 102 and a second nerve stump 104 via sutures (106, 108). As illustrated in FIG. 1B, the sutures (106, 108) are threaded through each nerve stump (102, 104) to pull the respective nerve stump (102, 104) inside the hollow portion of the construct 100 and secure the construct 100 in place. The sutures (106, 108) may be made from a variety of materials suitable for an epineural grasping stitch (e.g., single 8-0 or 9-0 nylon suture).

In certain embodiments, the neural repair construct is of sufficient size and shape to be applied onto or around a nerve. The neural repair construct thickness may vary depending on the type of membrane, the number of membrane layers, and the size of the damaged nerve in need of repair. In certain embodiments, the neural repair construct thickness is minimized to aid in the placement of the construct, yet robust enough to remain attached to the nerve stumps after placement, thereby maintaining an open lumen throughout the process of repair.

The inside diameter of the neural repair construct may also vary according to the size of the damaged nerve in need of repair. In certain embodiments, the inside diameter is from about 1 mm to about 10 mm. The length of the construct may also vary depending on the distance required to bridge a gap between nerve ends. In certain embodiments, the construct is from about 1 cm to about 10 cm in length.

The invention further relates to methods for aseptically processing amniotic and chorionic membranes to produce a material that may be used to prepare a neural repair construct. To obtain the human birth tissue material needed to prepare a neural repair construct, potential human birth tissue donors providing informed consent are pre-screened during an examination of pre-natal medical records and blood test results. A comprehensive medical history and behavior risk assessment is obtained from the donor prior to donation incorporating U.S. Public Health Service guidelines. Discussions with the physician(s) and/or the donor mother are conducted to identify circumstances that may lead to the exclusion of the donor or donated tissue. Additionally, a physical exam is performed on the donor to determine whether there is evidence of high risk behavior or infection and to determine the overall general health of the donor.

Infectious disease testing of donor blood specimens is performed for each tissue donor on a specimen collected at the time of donation or within seven days prior to or after donation. Exemplary infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc-total, meaning IgG and IgM); antibodies to the hepatitis C virus (anti-HCV); NAT for HCV; antibodies to human T-lymphotropic virus type I and type II (anti-HTLV-I and anti-HTLV-II); and syphilis (a non-treponemal or treponemal-specific assay may be performed).

Human birth tissue is preferably recovered from a full-term aseptic Cesarean delivery of a newborn. Alternatively, human birth tissue is recovered from a full-term vaginal delivery of a newborn. The placental organ, including the placental globe, umbilical cord, associated membranes (chorionic membrane and amniotic membrane), and other gelatins, fluids, cells and extracellular matrix can be recovered from a seronegative, healthy human after the newborn is removed. The placental globe, umbilical cord, and other gelatins, fluids, cells and extracellular matrix can be removed and discarded.

The membrane giving rise to the neural repair construct as described herein may be produced by processing human birth tissue according to the steps provided herein. Processing does not change the physical properties of the resulting membrane so as to yield the membrane tissue unacceptable for clinical use. Instruments, solutions, and supplies coming into contact with tissue during the processing of the placental tissue are sterile. All surfaces coming in contact with tissue intended for transplant are either sterile or draped using aseptic technique.

Throughout processing, the orientation of the particular membrane may be identified. Either the fetal side or the maternal side of the membrane may be used depending upon the specific use or procedure that is being performed.

Figure 2:
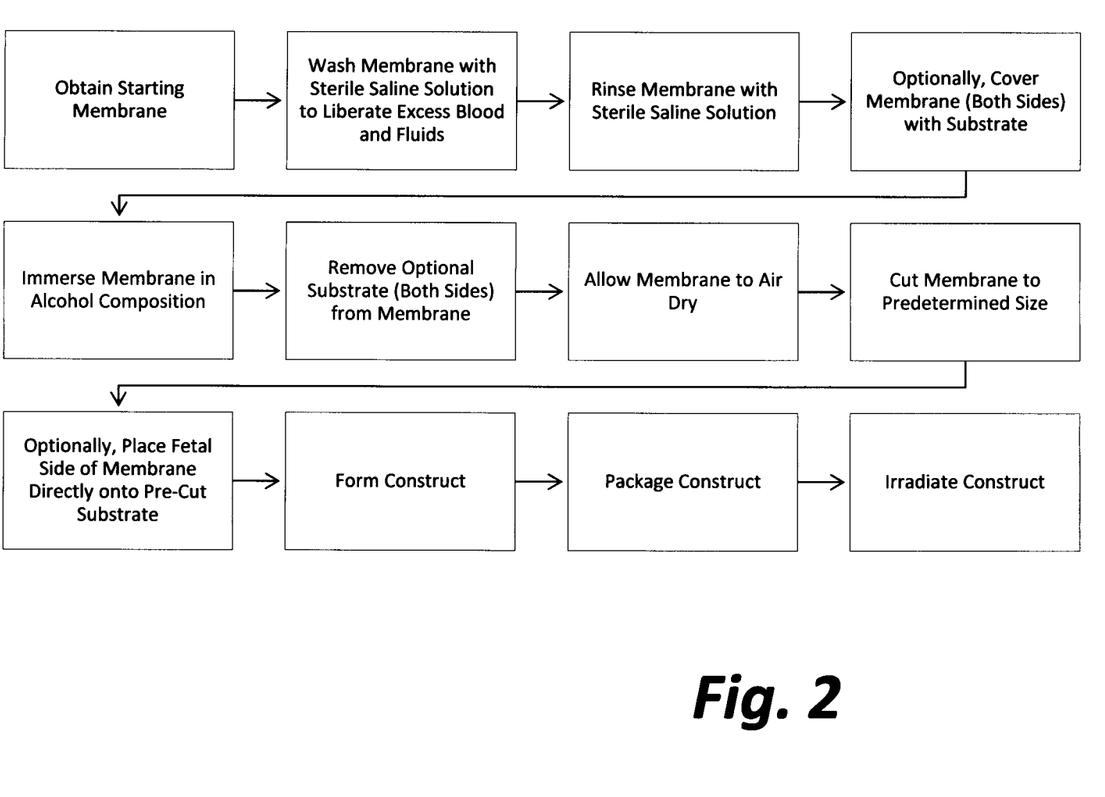
FIG. 2 illustrates a method of preparing a neural repair construct from human birth tissue material according to one embodiment.
Figure 3:
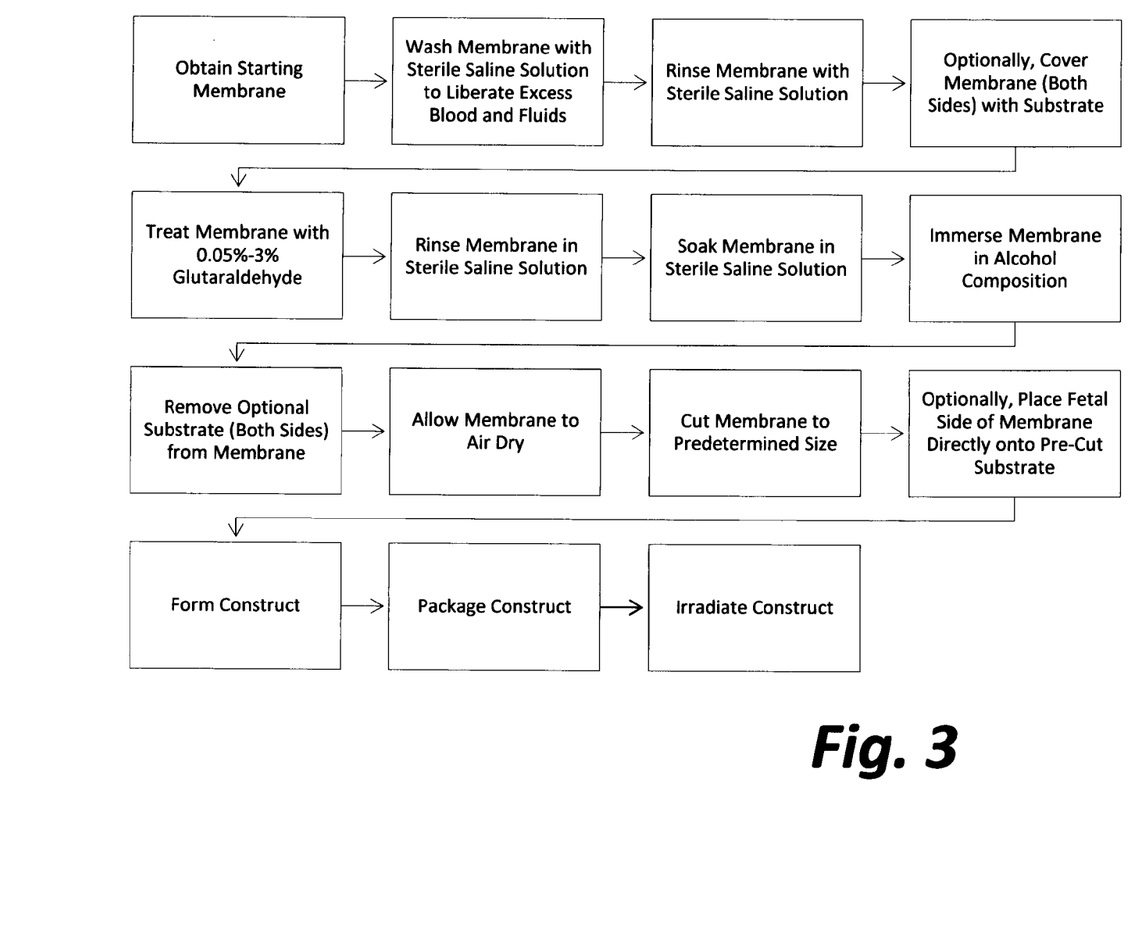
FIG. 3 illustrates a method of preparing a neural repair construct from human birth tissue material according to one embodiment.
Figure 4:
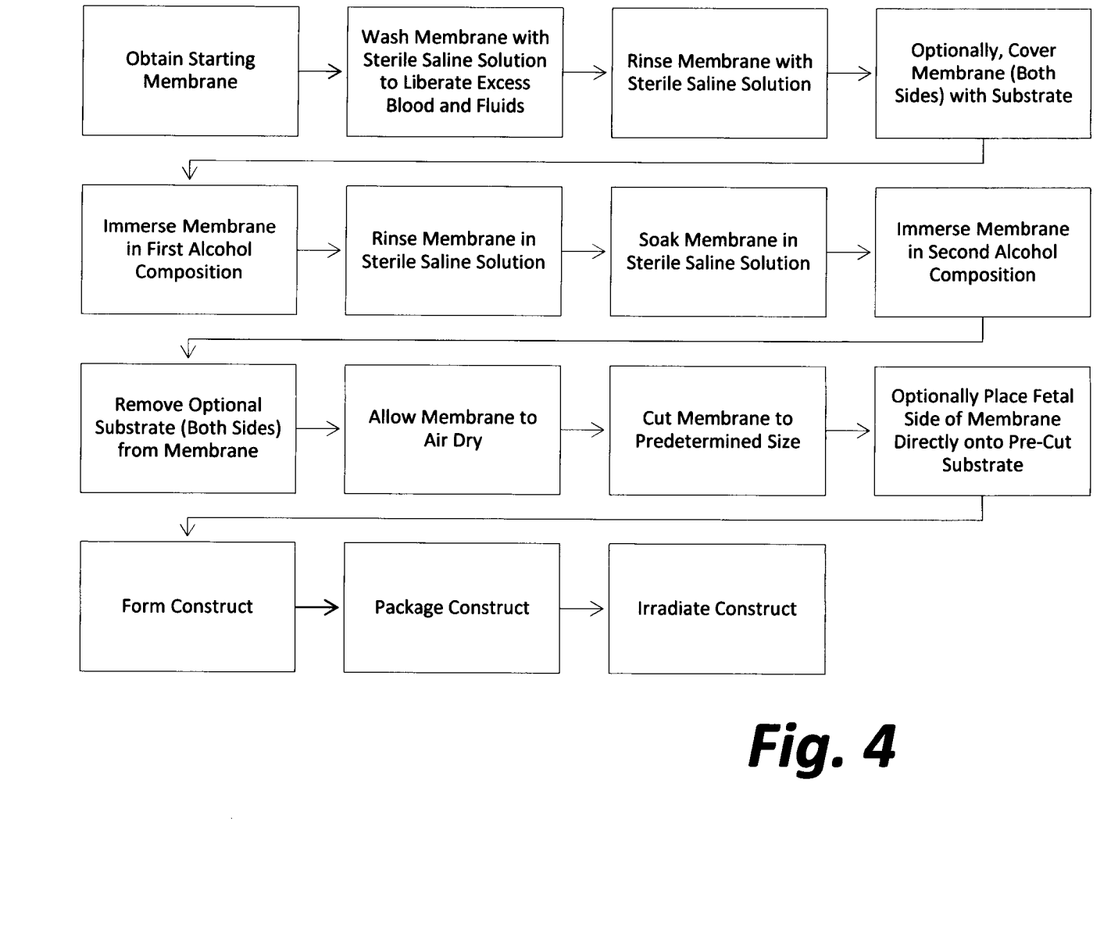
FIG. 4 illustrates a method of preparing a neural repair construct from human birth tissue material according to one embodiment.

According to the embodiment as illustrated in FIG. 2, FIG. 3 or FIG. 4, the neural repair construct is prepared by first obtaining amniotic membrane, chorionic membrane, or both amniotic and chorionic membrane from a seronegative, healthy human via cesarean section or vaginal delivery as described herein. In particular embodiments where only the amniotic membrane is chosen for further processing, the chorionic membrane can be removed by blunt dissection. For example, the chorionic membrane may be removed by applying finger pressure and sliding it off of the amniotic membrane using as little pressure as possible to avoid tearing of the amnion. The chorionic membrane and any excess tissue can be discarded.

The recovered amniotic membrane, chorionic membrane, or both amniotic and chorionic membrane may be initially stored in a sterile saline solution at a temperature between about 1° C. to about 10° C. for a period of up to about 120 hours prior to further processing. According to one embodiment, the sterile saline solution comprises from about 0.9% to about 20% NaCl, preferably 15% NaCl.

Optionally, the membrane may be treated with an oxidizer. In one embodiment, the oxidizer is hydrogen peroxide, which is also used as a sterilant and to enhance the solubilization of lipids. Such a treatment process includes the steps of:

(a) rinsing the membrane with 120 ml of sterile isotonic solution per gram of membrane for a period of up to about ten minutes;

(b) treating the membrane with 60 ml of hydrogen peroxide per gram of membrane for a period of up to about ten minutes; and (c) rinsing the membrane with 120 ml of sterile isotonic solution per gram of membrane for a period of up to about ten minutes.

The membrane is then immersed in a basin containing a sterile saline solution. According to one embodiment, the sterile saline solution includes typically from about 0.9% to about 20% NaCl.

Excess blood and fluids may be liberated from the membrane by gently stirring or swirling the fluid in a circular motion in the basin or by placing the basin on a shaker. The membrane can then be rinsed with a sterile saline solution. In one embodiment, the sterile saline solution includes NaCl in a concentration range of about 0.9% to about 20%. In one embodiment, the membrane may be rinsed in bowls or trays of sufficient size to allow the membrane to be spread out to improve the rinse coverage. Sufficient saline solution is utilized to ensure that the membrane is completely immersed. The saline is then decanted into a discard basin.

Multiple saline rinse cycles may be performed. In one embodiment, the membrane is rinsed for two or more separate rinse cycles, with each rinse cycle lasting for a maximum of five minutes. The membrane can be optionally covered with a substrate on both the fetal membrane side and the maternal membrane side. Appropriate substrates include, but are not limited to, a sterile mesh or polymer mesh of adequate size and shape for covering each side of the membrane.

According to the embodiment as illustrated in FIG. 3, the membrane is then optionally immersed in a preservative solution for a period of time of typically up to about twenty minutes. The preservative solution includes typically from about 0.05% to about 3% glutaraldehyde and, preferably, about 0.1% glutaraldehyde. The membrane may then be optionally stirred or swirled at a temperature of typically about 22° C. (±1-5° C.). When present, glutaraldehyde leads to collagen cross-linking, which, in turn, leads to a significant increase in the biomechanical strength of the membrane. Additionally, the handling characteristics of the membrane are improved after glutaraldehyde treatment because the membrane is more rigid and does not fold over onto itself. Glutaraldehyde cross-linking also prohibits fast resorption of the membrane by the body after implantation. The glutaraldehyde treatment is preferably performed in a bowl or tray of sufficient size to allow the membrane to spread out in order to maximize exposure of the tissue to the glutaraldehyde solution. Sufficient glutaraldehyde solution should be used to immerse the membrane in the solution. Typically, a minimum of about 400 ml of glutaraldehyde solution is used.

According to the alternative embodiment as illustrated in FIG. 4, the preservative solution may optionally include from about 90% to about 100% ethanol (i.e., in the absence of glutaraldehyde (see FIG. 4—referred to as "first alcohol composition")). In certain embodiments, the alcohol composition includes about 95.5% ethanol. In other embodiments, the alcohol composition includes about 100% ethanol. A neural repair construct produced according to the embodiment of FIG. 4 will be resorbed more quickly by the body (as opposed to glutaraldehyde treatment followed by alcohol treatment).

The membrane is then optionally rinsed with a sterile saline solution. Alternatively, the membrane is rinsed multiple times with a sterile saline solution. According to one embodiment, the sterile saline solution includes typically from about 0.9% to about 20% of NaCl. The membrane can then be optionally soaked in a sterile saline solution. According to one embodiment, the sterile saline solution includes typically from about 0.9% to about 20% of NaCl. According to one embodiment, soaking is conducted for a maximum period of about 35 minutes.

As illustrated in each of the embodiments of FIGS. 2, 3, and 4, the membrane is then immersed in an alcohol composition for a period of typically from about 24 hours to about 384 hours (referred to as "second alcohol composition" in FIG. 4). The alcohol composition includes about 90% to about 100% ethanol. In certain embodiments, the alcohol composition includes about 95.5% ethanol. In other embodiments, the alcohol composition includes about 100% ethanol. Treatment of the membrane within a particular alcohol concentration range for the particular timeframe at this step in the process has yielded unexpected results related to the handling characteristics. One of ordinary skill in the art appreciates the difficulty of handling and manipulating amniotic and chorionic tissue during manipulation and application. Specifically, existing amniotic and chorionic grafts are difficult to place over or around a specific tissue, particularly because these grafts fold back over on themselves ("wrinkling"), rendering proper placement and positioning very challenging. When treated with the aforementioned alcohol composition for the particular timeframe, the resulting neural repair construct experiences further cross-linking which aids in the handling characteristics of the neural repair construct. The alcohol-treated membrane does not "wrinkle" and allows for easy manipulation and formation of a neural repair construct. Furthermore, the alcohol treatment is multi-functional, providing a means of sterilization, preservation, and chemical dehydration for the graft, in addition to serving as a radioprotectant for the graft prior to terminal irradiation.

The optional substrate can then be removed from both the fetal membrane side and the maternal membrane side. The alcohol-treated membrane can then be spread on a flat, dry and sterile surface. The membrane is then allowed to air dry completely at ambient temperature for a period of up to typically about three hours. The membrane can then be cut to the desired size for forming a neural repair construct. In certain embodiments, the membrane can be cut into strips of any desired size by a rotary-type cutting tool. A grooved or similarly indicated cutting board may be used to aid in cutting a straight and correctly-sized neural repair construct. In another embodiment, the neural repair construct is cut by free hand using a scalpel and ruler to achieve the desired size.

If desired, the membrane may be treated to provide for the delivery of a variety of antibiotics, anti-inflammatory agents, growth factors and/or other specialized proteins or small molecules that may be advantageous in neural repair.

Figure 5:
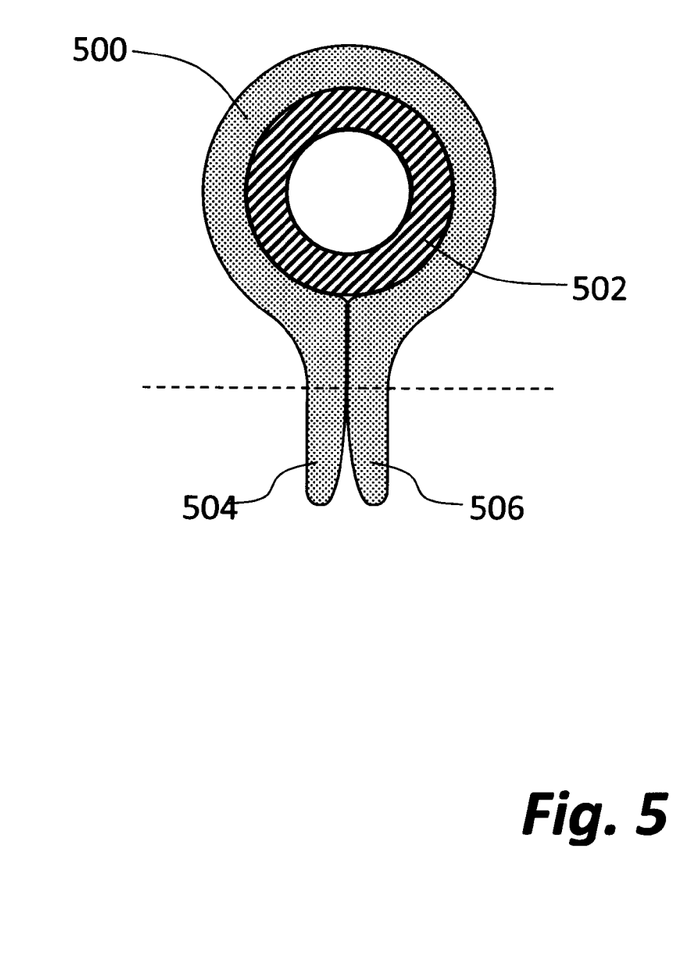
FIG. 5 illustrates the formation of a neural repair construct according to one embodiment.

According to one embodiment, the appropriately-sized membrane may be immersed in an alcohol composition. The alcohol composition includes about 90% to about 100% ethanol. In certain embodiments, the alcohol composition includes about 95.5% ethanol. In other embodiments, the alcohol composition includes about 100% ethanol. According to one embodiment, immersion is conducted for a maximum period of about five minutes. As illustrated in FIG. 5, the membrane(s) 500 as described herein can be wrapped around a mandrel 502 such that an opposing first end 504 and second end 506 overlap. The membrane may be dried by any method commonly known in the art, including, but not limited to, air drying, lyophilization, vacuum oven dehydration, non-vacuum oven dehydration or incubator dehydration. The inside diameter of the resulting construct may be varied by adjusting the outside diameter of the mandrel 502. As illustrated in FIG. 5 by the horizontal dotted line, the opposing ends (504, 506) may be cut or snipped to form a substantially cylindrical, hollow construct. The thickness of the neural repair construct can be optionally adjusted by turning the construct on an appropriate cutting tool (e.g., lathe) and trimming a portion of the exterior surface.

The neural repair construct can be optionally wrapped, coated, or otherwise covered with a material or composition that is not resorbed by the body. In certain embodiments, the construct can be optionally wrapped with a mesh fabric (e.g., DACRON) around the exterior surface of the construct.

In one embodiment, the neural repair construct can be cryopreserved according to methods commonly used in the art. The neural repair construct can be soaked in cryoprotectant prior to cryopreservation. In one embodiment, the cryoprotectant is one commonly used in the industry, such as, for example, dimethyl sulfoxide (DMSO). In a preferred embodiment, the cryoprotectant is an amnion control rate freeze solution comprising typically about 44% volume of Plasma Lyte-A, typically about 36% volume of human albumin 25% solution, and typically about 20% volume of dimethyl sulfoxide. In another embodiment, the cryoprotectant is a commercially available cryoprotectant such as Synth-a-Freeze® available from Invitrogen. In one embodiment, cryopreservation is achieved using a controlled rate freezer, resulting in a 1° C. rate from nucleation to −35° C. and a 10° C. per minute cooling rate to a −90° C. end temperature. However, any cryopreservation method commonly known in the art may be used.

The construct can then be packaged. In certain embodiments, the neural repair construct is packaged in a dry state. In other embodiments, the neural repair construct is packaged in a wet state, including, but not limited to, sterile water, crystalloids, ethanol, or another sterilizing, preserving or storage agent. The packaging can facilitate the handling of the neural repair construct, namely maintaining and identifying the orientation of the fetal and maternal side of the neural repair construct for the user. The packaging may also promote storage of the neural repair construct.

In a preferred embodiment, the packaged neural repair construct can be terminally sterilized using irradiation. In one embodiment, an electron beam irradiation is applied in an amount up to about 45 kGy. The sterilized neural repair construct may be stored for up to typically about two years from the date of processing. In one embodiment, the neural repair construct may be stored under proper conditions for as much as about five years following processing. The sterilized neural repair construct may be stored in any container suitable for long-term storage. Preferably, the sterilized neural repair construct is stored in a sterile double peel-pouch package.

If desired, the neural repair construct may be utilized with at least one composition or device for delivering, fastening or fixing the neural repair construct on or around a nerve. Exemplary compositions include, but are not limited to, tissue glue or tissue adhesive, fibrin glue, fibrinogen glue, hydrogel tissue glue, chondroitin sulfate aldehyde, or natural proteins. Exemplary devices include, but are not limited to, sutures or forceps.

A kit for use by a medical professional is also provided. According to one embodiment, the kit includes one or more packaged and sterilized neural repair constructs as provided herein and at least one set of instructions. The kit may further include at least one composition or device for delivering, fastening or fixing the neural repair construct on or around a nerve. The kit may further include a container adapted to accommodate the aforementioned components while preserving the neural repair construct as per applicable Food and Drug Administration guidelines.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

Having generally described the present invention, a further understanding can be obtained by reference to the examples provided herein for purposes of illustration only and are not intended to be limiting.

Example 1

Representative samples of final product from four production lots #1, #2, #3 and #4 manufactured according to the methods of FIG. 3 were tested for residual glutaraldehyde and residual ethanol by gas chromatography, analytical methods EPA 8015M, CAS No. 111-30-8 and EPA 8260B, CAS No. 64-17-5, respectively. Samples were sent to Nelson Laboratories, Inc., 6280 South Redwood Road Salt Lake City, Utah 84123, a GLP qualified microbiology laboratory registered with the FDA and third-party accredited to ISO 17025 standards. The results are summarized in Table 1 and Table 2 below.

Samples from four production lots #1, #2, #3 and #4 were tested for residual glutaraldehyde by gas chromatography, analytical methods EPA 8015M, CAS No. 111-30-8 as follows:

Three representative samples of final product (2 cm×2 cm each) from production lot #1 included amniotic membranes that had been treated with a 0.1% glutaraldehyde composition for a period of 15 minutes and had been immersed in an alcohol composition comprising 95.5% ethanol for a period of 24 hours.

Zero headspace extraction was performed with double deionized water as the vehicle extractant. Extraction vessels were tumbled during the entire extraction process. For production lot #1, the three samples were pooled, and a test article was extracted with a weight of 0.046 g and fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was analyzed by gas chromatography for glutaraldehyde determination. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No glutaraldehyde was detected at the reported detection limit (1.0 mg/L) for production lot #1.

One sample of final product (4 cm×4 cm) from production lot #2 included an amniotic membrane that had been treated with a 0.1% glutaraldehyde composition for a period of 15 minutes and had been immersed in an alcohol composition comprising 95.5% ethanol for a period of 24.1 hours.

Zero headspace extraction was performed with double deionized water as the vehicle extractant. Extraction vessels were tumbled during the entire extraction process. For production lot #2, one test article was extracted with a weight of 0.051 g and fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was analyzed by gas chromatography for glutaraldehyde determination. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No glutaraldehyde was detected at the reported detection limit (1.0 mg/L) for production lot #2.

Two representative samples of final product (2 cm×6 cm each) from production lot #3 included amniotic membranes that had been treated with a 0.1% glutaraldehyde composition for a period of 15 minutes and had been immersed in an alcohol composition comprising 95.5% ethanol for a period of 41.3 hours.

Zero headspace extraction was performed with double deionized water as the vehicle extractant. Extraction vessels were tumbled during the entire extraction process. For production lot #3, the two samples were pooled, and a test article was extracted with a weight of 0.069 g and a fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was analyzed by gas chromatography for glutaraldehyde determination. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No glutaraldehyde was detected at the reported detection limit (1.0 mg/L) for production lot #3.

One sample of final product (4 cm×4 cm) from production lot #4 included an amniotic membrane that had been treated with a 0.1% glutaraldehyde composition for a period of 15 minutes and had been immersed in an alcohol composition comprising 95.5% ethanol for a period of 114.7 hours.

Zero headspace extraction was performed with double deionized water as the vehicle extractant. Extraction vessels were tumbled during the entire extraction process. For production lot #4, one test article was extracted with a weight of 0.037 g and fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was analyzed by gas chromatography for glutaraldehyde determination. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No glutaraldehyde was detected at the reported detection limit (1.0 mg/L) for production lot #4.

Samples from the same four production lots #1, #2, #3 and #4 were tested for residual ethanol by gas chromatography, analytical method EPA 8260B, CAS No. 64-17-5, as follows:

Three representative samples of final product (2 cm×2 cm each) from production lot #1 included amniotic membranes that had been treated with a 0.1% glutaraldehyde composition for a period of 15 minutes and had been immersed in an alcohol composition comprising 95.5% ethanol for a period of 24 hours.

Zero headspace extraction was performed with double deionized water as the vehicle extractant. Extraction vessels were tumbled during the entire extraction process. For production lot #1, the three samples were pooled, and a test article was extracted with a weight of 0.05 g and fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No ethanol was detected at the reported detection limit (0.5 mg/L) for production lot #1.

One sample of final product (4 cm×4 cm) from production lot #2 included an amniotic membrane that had been treated with a 0.1% glutaraldehyde composition for a period of 15 minutes and had been immersed in an alcohol composition comprising 95.5% ethanol for a period of 24.1 hours.

Zero headspace extraction was performed with double deionized water as the vehicle extractant. Extraction vessels were tumbled during the entire extraction process. For production lot #2, one test article was extracted with a weight of 0.04 g and fluid amount of 50 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No ethanol was detected at the reported detection limit (0.5 mg/L) for production lot #2.

Two samples of final product (4 cm×4 cm and 2 cm×6 cm) from production lot #3 included amniotic membranes that had been treated with a 0.1% glutaraldehyde composition for a period of 15 minutes and had been immersed in an alcohol composition comprising 95.5% ethanol for a period of 41.3 hours.

Zero headspace extraction was performed with double deionized water as the vehicle extractant. Extraction vessels were tumbled during the entire extraction process. For production lot #3, the two samples were pooled, and a test article was extracted with a weight of 0.08 g and fluid amount of 50 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No ethanol was detected at the reported detection limit (0.5 mg/L) for production lot #3.

Two samples of final product (4 cm×4 cm each) from production lot #4 included amniotic membranes that had been treated with a 0.1% glutaraldehyde composition for a period of 15 minutes and had been immersed in an alcohol composition comprising 95.5% ethanol for a period of 114.7 hours.

Zero headspace extraction was performed with double deionized water as the vehicle extractant. Extraction vessels were tumbled during the entire extraction process. For production lot #4, the two samples were pooled, and a test article was extracted with a weight of 0.09 g and fluid amount of 50 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No ethanol was detected at the reported detection limit (0.5 mg/L) for production lot #4.

TABLE 1

Glutaraldehyde Determination for Production Lots #1, #2, #3 and #4

| Production Lot | Total Time in Glutaraldehyde | Weight of Sample | Volume of Fluid | Starting Extraction Temperature | Ending Extraction Temperature | Duration of Extraction | Sample Results |
|---|---|---|---|---|---|---|---|
| 1 | 15 Minutes | 0.046 g | 100 mL | 22° C. | 23° C. | 24 Hours | ND* |
| 2 | 15 Minutes | 0.051 g | 100 mL | 22° C. | 23° C. | 24 Hours | ND* |
| 3 | 15 Minutes | 0.069 g | 100 mL | 22° C. | 23° C. | 24 Hours | ND* |
| 4 | 15 Minutes | 0.037 g | 100 mL | 22° C. | 23° C. | 24 Hours | ND* |

*ND = Not Detected at the Minimum Reporting Limit (1.0 mg/L)

TABLE 2

Ethanol Determination for Production Lots #1, #2, #3 and #4

| Production Lot | Total Time in Ethanol | Weight of Sample | Volume of Fluid | Starting Extraction Temperature | Ending Extraction Temperature | Duration of Extraction | Sample Results |
|---|---|---|---|---|---|---|---|
| 1 | 24.0 Hours | 0.05 g | 50 mL | 22° C. | 23° C. | 24 Hours | ND* |
| 2 | 24.1 Hours | 0.04 g | 50 mL | 22° C. | 23° C. | 24 Hours | ND* |
| 3 | 41.3 Hours | 0.08 g | 50 mL | 22° C. | 23° C. | 24 Hours | ND* |
| 4 | 114.7 Hours | 0.09 g | 50 mL | 22° C. | 23° C. | 24 Hours | ND* |

*ND = Not Detected at the Minimum Reporting Limit (0.5 mg/L)

Example 2

Three representative samples of final product for each of three production lots manufactured according to the methods of FIG. 2 were tested for residual ethanol by gas chromatography, analytical method EPA 8260B, CAS No. 64-17-5. Samples were sent to Nelson Laboratories, Inc., 6280 South Redwood Road Salt Lake City, Utah 84123, a GLP qualified microbiology laboratory registered with the FDA and third-party accredited to ISO 17025 standards.

The three samples submitted for testing from production lot #5 (2 cm×3 cm; 2 cm×3 cm; and 1.5 cm×2 cm) included amniotic membranes that had been immersed in an alcohol composition comprising 95.5% ethanol for a period of 110 hours. The three samples submitted for testing from production lot #6 (2 cm×3 cm each) included amniotic membranes that had been immersed in an alcohol composition comprising 95.5% ethanol for a period of 25.5 hours. The three samples submitted for testing from production lot #7 (2 cm×3 cm each) included amniotic membranes that had been immersed in an alcohol composition comprising 95.5% ethanol for a period of 24.9 hours.

Zero headspace extraction was performed with double deionized water as the vehicle extractant. Extraction vessels were tumbled during the entire extraction process. For each of the three production lots, the samples were pooled, and one test article was extracted with a weight of 0.05 g and fluid amount of 50 ml. The starting extraction temperature was 22° C. and the ending extraction temperature was 23° C. The extractions lasted twenty-four hours. All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

The certificates of analyses for production lots #5, #6 and #7 indicated no detectable amounts of ethanol at the minimum reporting limit (0.5 mg/L). The results are summarized in Table 3 below.

TABLE 3

Ethanol Determination for Production Lots #5, #6 and #7

| Production Lot | Total Time in Ethanol | Weight of Sample | Volume of Fluid | Starting Extraction Temperature | Ending Extraction Temperature | Duration of Extraction | Sample Results |
|---|---|---|---|---|---|---|---|
| 5 | 110.0 Hours | 0.05 g | 50 mL | 22° C. | 23° C. | 24 Hours | ND* |
| 6 | 25.5 Hours | 0.05 g | 50 mL | 22° C. | 23° C. | 24 Hours | ND* |
| 7 | 24.9 Hours | 0.05 g | 50 mL | 22° C. | 23° C. | 24 Hours | ND* |

*ND = Not Detected at the Minimum Reporting Limit (0.5 mg/L)

We claim:

1. A method of repairing a severed nerve, comprising the steps of:
   providing a neural repair construct comprising:
   at least one cross-linked amniotic membrane, or
   at least one cross-linked chorionic membrane, or
   at least one amniotic membrane, or
   at least one chorionic membrane, or
   any combination thereof;
   securing a first nerve stump of the severed nerve to a first end of the construct; and
   securing a second nerve stump of the severed nerve to a second, opposing end of the construct,
   wherein the membrane(s) is/are chemically dehydrated with a single ethanol composition for about 24 hours to about 384 hours, the ethanol composition comprising from about 90% to about 100% ethanol, and
   wherein the membrane(s) is/are terminally sterilized after chemical dehydration to form a neural repair construct.

2. The method of claim 1, wherein the steps of securing the first and second nerve stumps to the opposing ends of the construct are accomplished by at least one epineural grasping stitch.

3. The method of claim 1, wherein the neural repair construct is wrapped with a mesh fabric around an exterior surface of the construct.

4. The method of claim 1, wherein the neural repair construct is cryopreserved prior to use.

5. The method of claim 4, wherein the neural repair construct is cryopreserved in a control rate freeze solution comprising about 44% volume of Plasma Lyte-A, about 36% volume of human albumin 25% solution, and about 20% volume of dimethyl sulfoxide.

6. The method of claim 4, wherein the neural repair construct is cryopreserved by controlled rate freezing at a 10° C. per minute cooling rate to a −90° C. end temperature.

7. The method of claim 1, wherein the neural repair construct provides a protective conduit for axonal regrowth and regeneration across a nerve gap.

8. The method of claim 1, wherein the at least one cross-linked amniotic or chorionic membrane is cross-linked in a 0.1% glutaraldehyde cross-linking solution.

9. The method of claim 8, wherein the cross-linked amniotic or chorionic membrane is rinsed in a sterile saline solution after immersion in the 0.1% glutaraldehyde cross-linking solution.

10. The method of claim 1, wherein terminal sterilization is gamma irradiation or electron beam irradiation.

11. The method of claim 1, wherein the steps of securing the first and second nerve stumps to the opposing ends of the construct are accomplished with at least one composition selected from the group consisting of fibrin glue, fibrinogen glue, hydrogel tissue glue, chondroitin sulfate aldehyde, and natural proteins.

* * * * *